United States Patent
Millard et al.

(10) Patent No.: US 9,839,413 B2
(45) Date of Patent: Dec. 12, 2017

(54) DEVICE AND METHOD FOR CONDUCTING A PAP SMEAR TEST

(71) Applicants: Matthew D Millard, La Jolla, CA (US); Imran Jawaid, Hollywood, CA (US); Winston L Alexis, Plantation, FL (US)

(72) Inventors: Matthew D Millard, La Jolla, CA (US); Imran Jawaid, Hollywood, CA (US); Winston L Alexis, Plantation, FL (US)

( * ) Notice: Subject to any disclaimer, the term of this patent is extended or adjusted under 35 U.S.C. 154(b) by 0 days.

(21) Appl. No.: 13/942,239

(22) Filed: Jul. 15, 2013

(65) Prior Publication Data

US 2015/0018669 A1    Jan. 15, 2015

(51) Int. Cl.
*A61B 8/00* (2006.01)
*A61B 10/02* (2006.01)
*A61B 8/08* (2006.01)
*A61B 8/12* (2006.01)

(52) U.S. Cl.
CPC .......... *A61B 10/0291* (2013.01); *A61B 8/085* (2013.01); *A61B 8/12* (2013.01); *A61B 8/445* (2013.01); *A61B 2010/0216* (2013.01)

(58) Field of Classification Search
CPC ......... A61B 5/725; A61B 1/042; A61B 1/303; A61B 1/043; A61B 6/00; A61B 5/0059; A61B 10/02; A61B 2010/0216; A61B 8/08; A61B 8/00
See application file for complete search history.

(56) References Cited

U.S. PATENT DOCUMENTS

| | | | | |
|---|---|---|---|---|
| 2001/0047136 A1* | 11/2001 | Domanik et al. | ............ | 600/473 |
| 2009/0082695 A1* | 3/2009 | Whitehead | .................... | 600/562 |
| 2013/0079599 A1* | 3/2013 | Holmes et al. | ............... | 600/300 |

* cited by examiner

*Primary Examiner* — Joel Lamprecht
(74) *Attorney, Agent, or Firm* — John R. Ross; John R. Ross, III

(57) ABSTRACT

A protective guide for protecting a cell extraction device used during a Pap smear. An access tunnel receives the cell extraction device and allows for access and movement of the cell extraction device. A protective chamber covers and protects the head of the cell extraction device as the cell extraction device is being removed and inserted from the patient's vagina. A protective guide connector attaches the protective guide to an imaging transducer. After inserted into the patient's vagina, the location of the patient's cervix is determined by utilization of the imaging transducer. Once the cervix is located the cell extraction device is pushed outward from the protective chamber so that the cell extraction device head contacts the cervix and then removes cells from the cervix. The cell extraction device head is then pulled back into the protective chamber and the protective guide is removed from the patient's vagina.

16 Claims, 7 Drawing Sheets

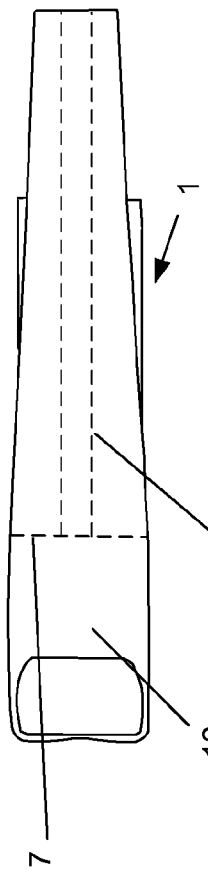
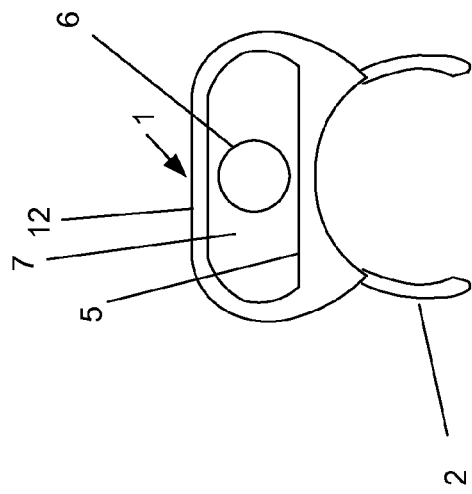
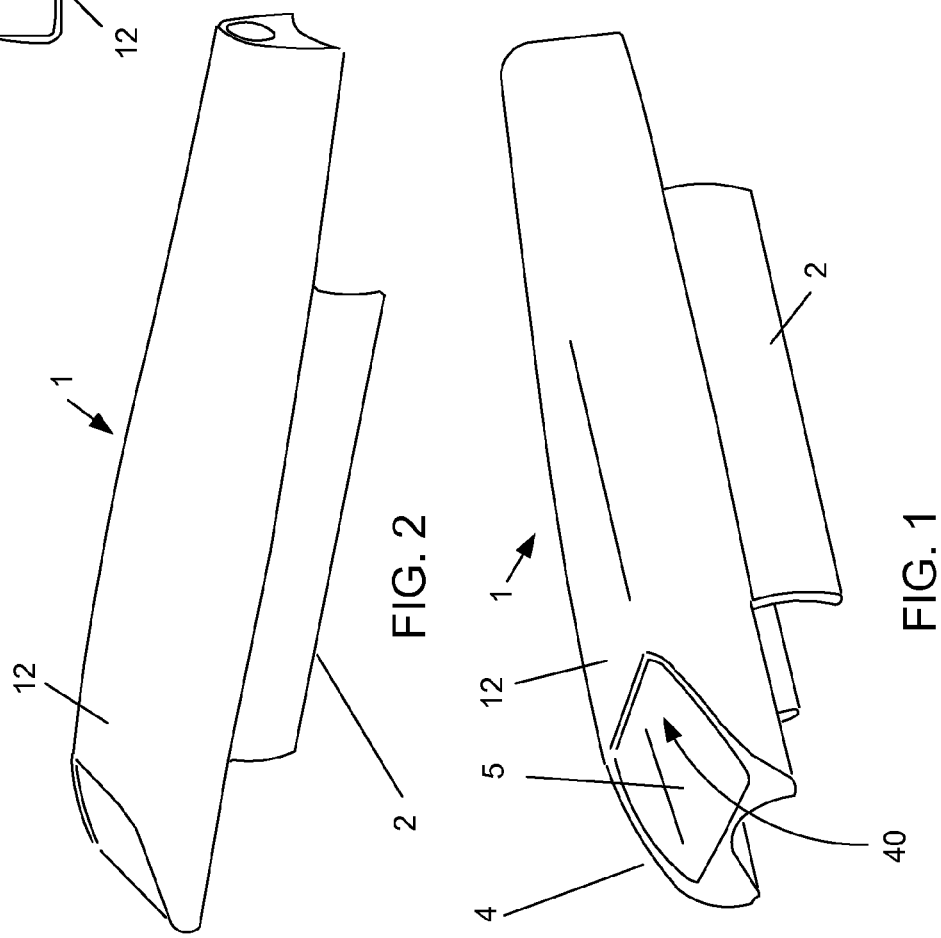

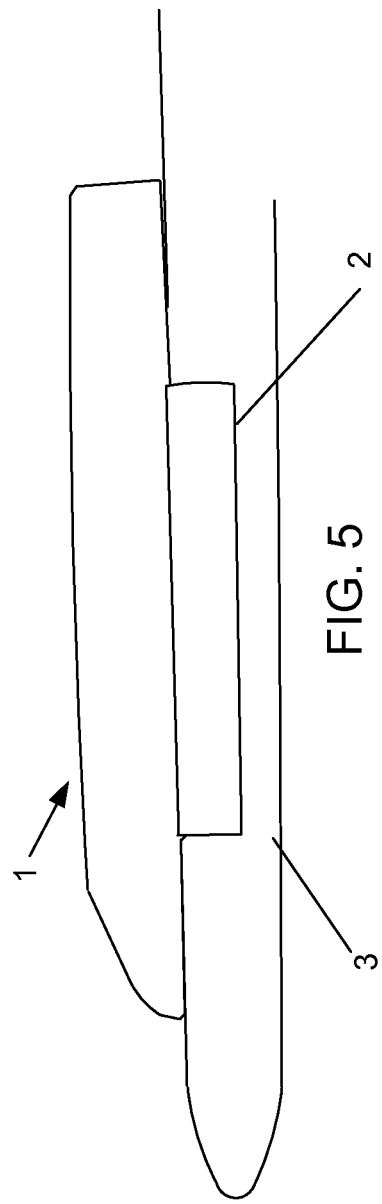
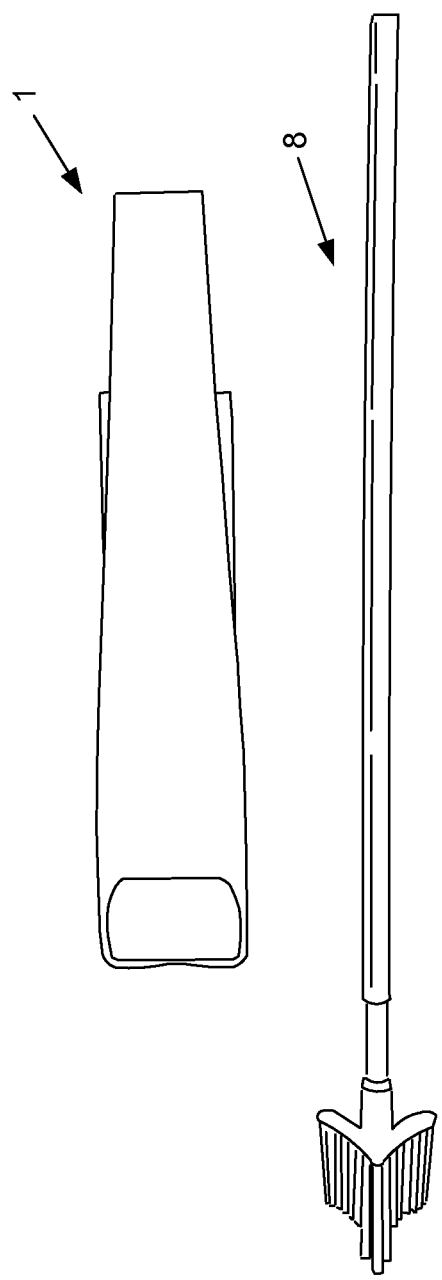

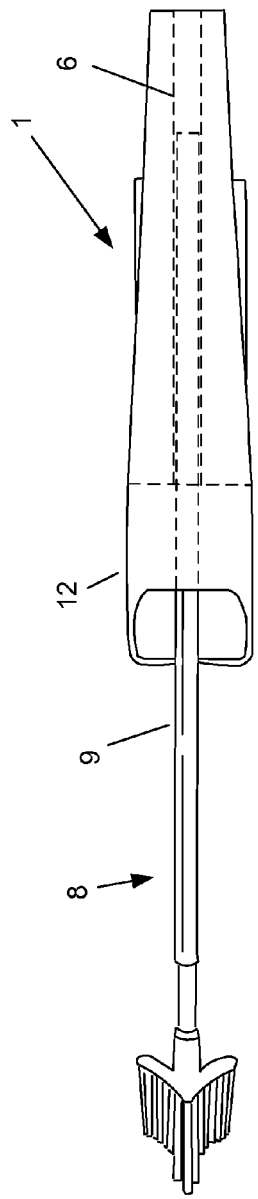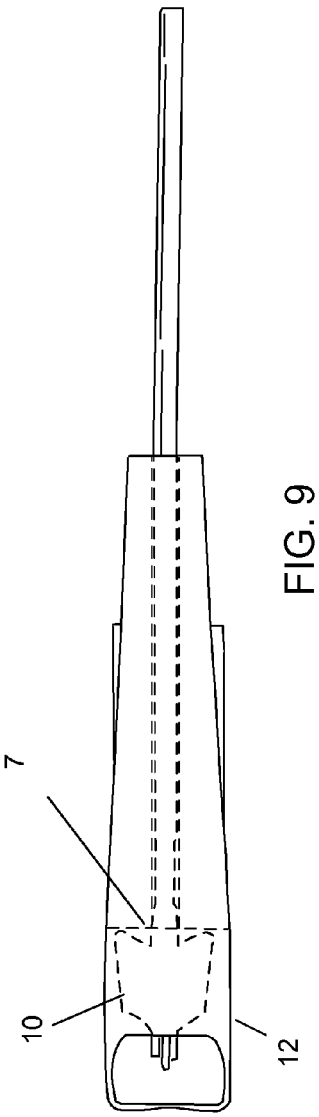

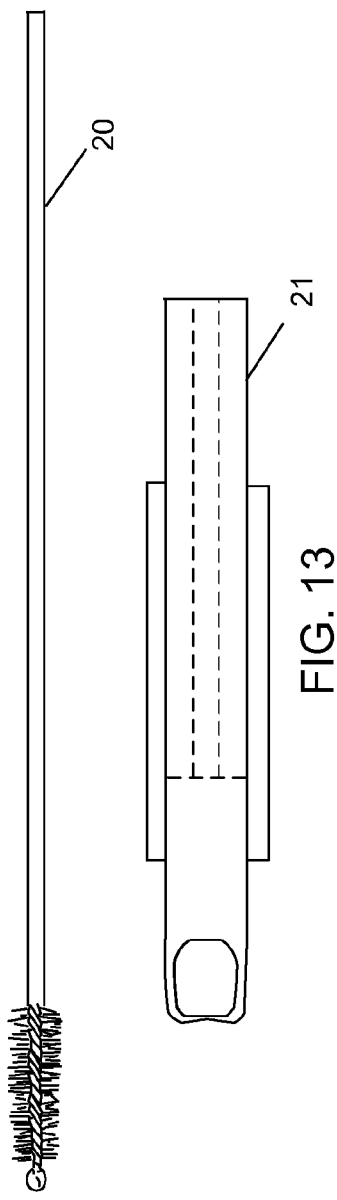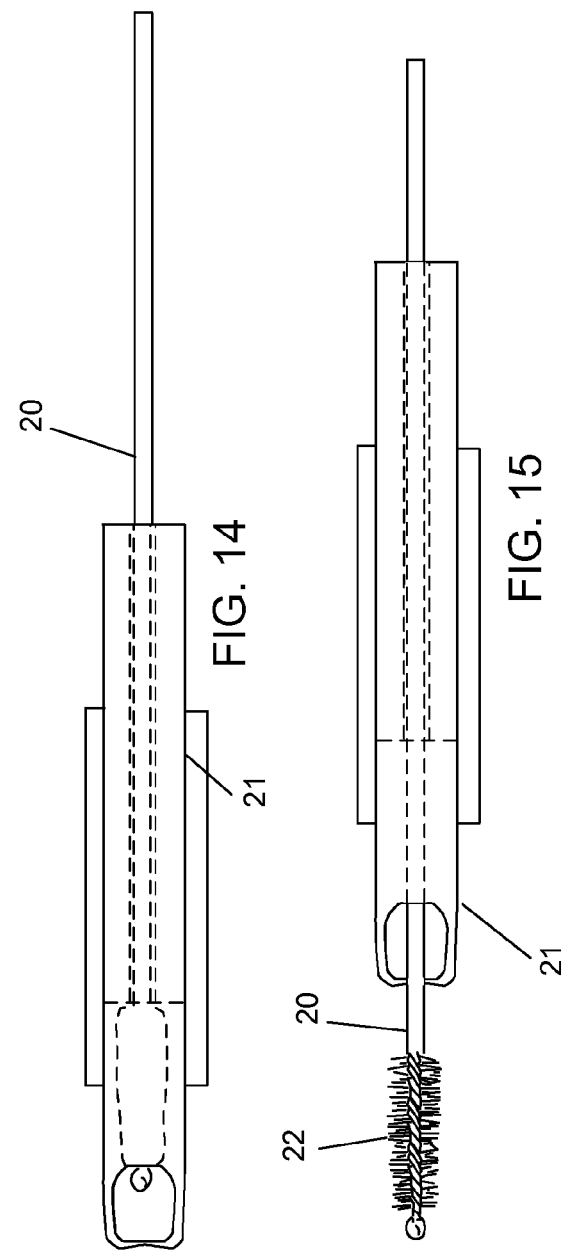

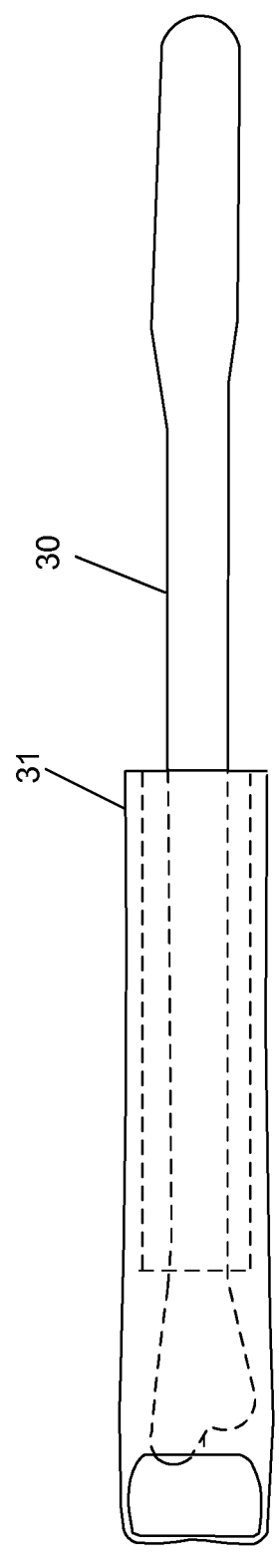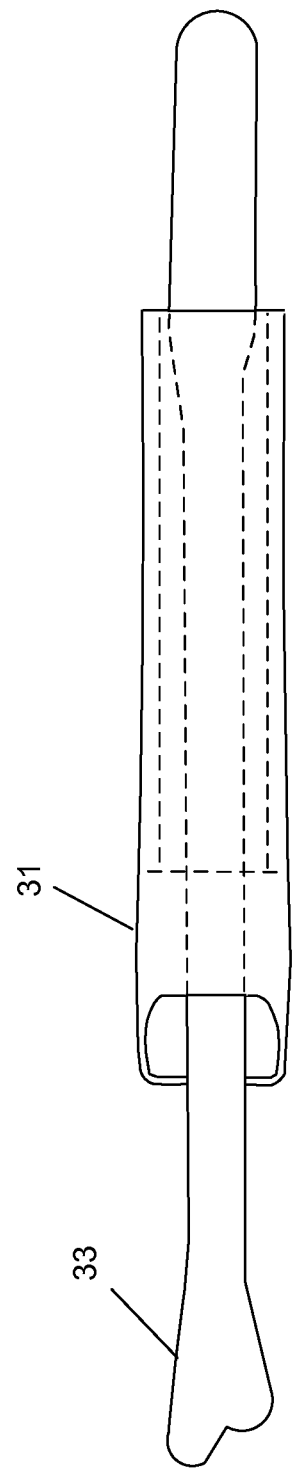
FIG. 16
FIG. 17

DEVICE AND METHOD FOR CONDUCTING A PAP SMEAR TEST

The present invention relates to medical devices and procedures, and in particular, to medical devices and procedures for conducting a Pap smear test.

BACKGROUND OF THE INVENTION

The Papanicolaou test (also called Pap smear, Pap test, cervical smear, or smear test) is a screening test used to detect potentially pre-cancerous and cancerous processes in the endocervical canal (transformation zone) of the female reproductive system.

A Pap smear is accomplished by usage of a cell extraction device such as a Pap smear spatula and Pap smear brush or alternatively by utilization of a Pap smear broom. In either case, the medical practitioner begins by inserting a speculum into the woman's vagina, which spreads the vagina open and allows access to the cervix. If using the spatula and brush, the medical practitioner then collects a sample of cells from the outer opening of the cervix by scraping it with the spatula. Then, an endocervical brush is rotated in the central opening of the cervix. Alternatively the medical practitioner may opt to use a plastic-fronded broom (Pap smear broom) in place of the spatula and brush. The cells are removed from the patient and are placed on a glass slide that is sent to a laboratory to be checked for abnormalities.

Speculum Problems

As stated above, the prior art method of conducting a Pap smear involves the use of a speculum to spread open the vagina. The utilization of the speculum can be extremely uncomfortable and painful to many women as the vagina is spread apart. Some women have even described the speculum as agonizing. The fear and apprehension associated with the speculum has unfortunately caused many women to delay the Pap smear test or, in some cases, to even avoid it entirely. This is unacceptable because it can allow preventable cancer to remain undiagnosed.

What is needed is a better device and method for conducting a Pap smear.

SUMMARY OF THE INVENTION

The present invention provides a protective guide for protecting a cell extraction device used during a Pap smear. An access tunnel receives the cell extraction device and allows for access and movement of the cell extraction device. A protective chamber covers and protects the head of the cell extraction device as the cell extraction device is being removed and inserted from the patient's vagina. A protective guide connector connects the protective guide to an imaging transducer. After inserted into the patient's vagina, the location of the patient's cervix is determined by utilization of the imaging transducer. Once the cervix is located the cell extraction device is pushed outward from the protective chamber so that the cell extraction device head contacts the cervix and removes cells from the cervix. The cell extraction device head is then pulled back into the protective chamber and the protective guide is removed from the patient's vagina.

BRIEF DESCRIPTION OF THE DRAWINGS

FIGS. 1-4 show a preferred embodiment of the present invention.

FIG. 5 shows a preferred protective guide connected to an imaging transducer.

FIG. 6 shows a top view of a preferred protective guide and a Pap smear broom.

FIGS. 7-12 show the utilization of a preferred embodiment of the present invention.

FIGS. 13-15 show another preferred embodiment of the present invention.

FIGS. 16-17 show another preferred embodiment of the present invention.

DETAILED DESCRIPTION OF THE PREFERRED EMBODIMENTS

Protective guide 1 (FIG. 1) allows for a more comfortable, more efficient Pap smear in that a Pap smear can now be conducted without the utilization of a speculum. The patient no longer has to experience the fear, pain and apprehension commonly associated with a Pap smear.

Figure 11:
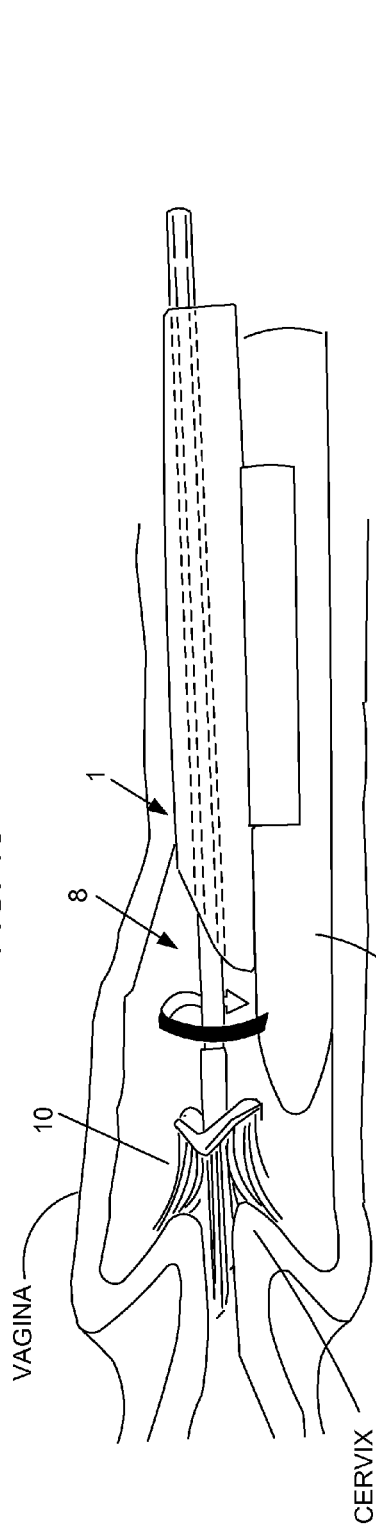
Figure 12:
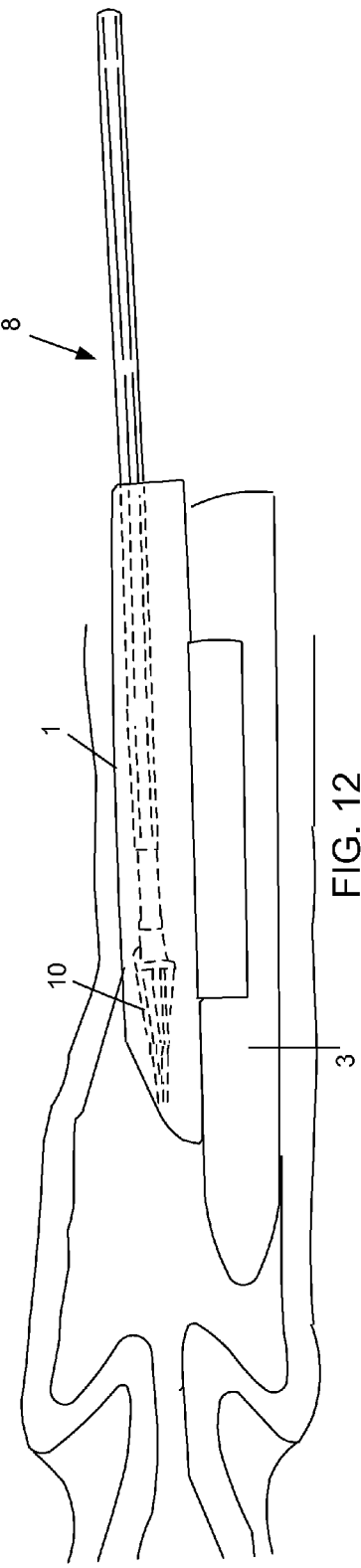

FIGS. 11 and 12 show preferred Pap smear broom 8 protected by protective guide 1 inserted into the vagina of a patient. Pap smear broom 8 is inserted into Pap smear protective guide 1. Protective guide 1 is attached to ultrasound probe 3. In FIG. 11, the medical examiner has located the cervix by utilization of ultrasound probe 3. The medical examiner has pushed Pap smear broom 8 outward so that broom head 10 is in contact with the cervix. The medical examiner is able to remove cells from the cervix for examination as shown. In FIG. 12 the medical examiner has pulled Pap smear broom 8 so that broom head 10 is now covered by the protective walls of protective guide 1. Protective guide 1 can now be withdrawn from the vagina.

Preferred Protective Guide

FIGS. 1-5 show a preferred embodiment of the present invention. FIGS. 1 and 2 show perspective views of protective guide 1. FIG. 3 shows a top view and FIG. 4 shows a front view of protective guide 1. Protective guide 1 includes connector 2 that allows for secure connection to an imaging transducer such as ultrasound probe 3 (FIG. 5). Protective guide 1 is preferably plastic and is preferably fabricated utilizing an injection molding process. Protective guide 1 includes slanted, low profile front section 4 to allow for easy and comfortable insertion into the vagina. Front section 4 includes flat broom support section 5 to support the Pap smear broom when the broom is held within protective guide 1. Hole 6 provides a tunnel that extends through protective guide 1 to allow access and movement for the Pap smear broom handle. Stop 7 is positioned within protective guide 1 as shown and stops the rearward motion of the paper smear broom as it is pulled within protective guide 1. When the Pap smear broom is fully inserted inside protective guide 1, the broom head will be contained within protective chamber 40 (FIG. 1) and covered by walls 12 on the sides and top and by support section 5 on the bottom.

Utilization of a Preferred Pap Smear Brush

FIG. 6 shows protective guide 1 placed adjacent to Pap smear broom 8.

In FIG. 7, the user has begun to insert Pap smear broom into protective guide 1.

In FIG. 8, handle 9 has been inserted part way through hole 6.

In FIG. 9, broom head 10 of Pap smear broom 8 has been stopped moving rearward by stop 7. Broom head 10 is now substantially covered by walls 12.

Figure 10:
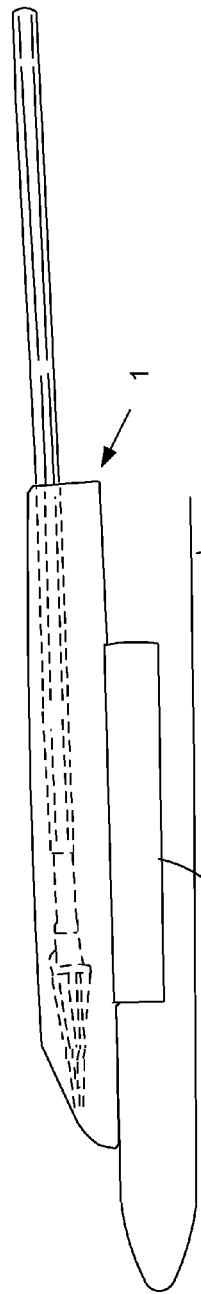

In FIG. 10 protective guide 1 is press fit onto ultrasound probe 3 and is held in place by gripping force between connector 2 and ultrasound probe 3. Pap smear broom 8 is now ready for insertion into the patient's vagina.

In FIG. 11 protective guide 1 attached to ultrasound probe 3 has been inserted into the patient's vagina. The image provided by ultrasound 3 is providing the medical examiner with a good image of the cervix. The medical examiner has pushed broom 8 outward slightly so that broom head 10 is able to contact the cervix. The central bristles of broom head 10 are inserted into the endocervical canal deep enough to allow the shorter bristles to fully contact the ectocervix. The medical examiner preferably pushes gently, and rotates brush section 10 in a clockwise direction five times.

In FIG. 12, the medical examiner has retracted broom head 10 inside protective guide 1. Broom head 10 is now covered and protected by the walls of protective guide 1. The medical examiner may now easily withdraw protective guide 1 and ultrasound probe 3.

Other Preferred Embodiments

FIGS. 1-12 show the utilization of protective guide 1 with a Pap smear broom. However, it should be understood that a similar protective guide can be utilized with other Pap smear cell extraction devices such as a Pap smear brush or Pap smear spatula.

FIG. 13 shows another preferred embodiment where Pap smear brush 20 is laid next to brush guide 21. As with the first preferred embodiment, Pap smear brush 20 is covered by the walls of brush guide 21 as it is attached to an ultrasound probe and inserted into a patient's vagina.

In FIG. 14 Pap smear brush 20 has been inserted into brush guide 21.

In FIG. 15 Pap smear brush 20 has been slightly pushed out of brush guide 21. Bristles 22 are now exposed and are able to contact a patient's cervix in a fashion similar to that described above.

FIG. 16 shows another preferred embodiment where Pap smear spatula 30 is inserted into brush guide 31. As with the first preferred embodiment, Pap smear brush 30 is covered by the walls of brush guide 31 as it is attached to a ultrasound probe and inserted into the patient's vagina.

In FIG. 17 head 33 of Pap smear spatula 30 has been slightly pushed out of brush guide 31. Head 33 is now exposed and is able to contact a patient's cervix in a fashion similar to that described above.

Figure 18:
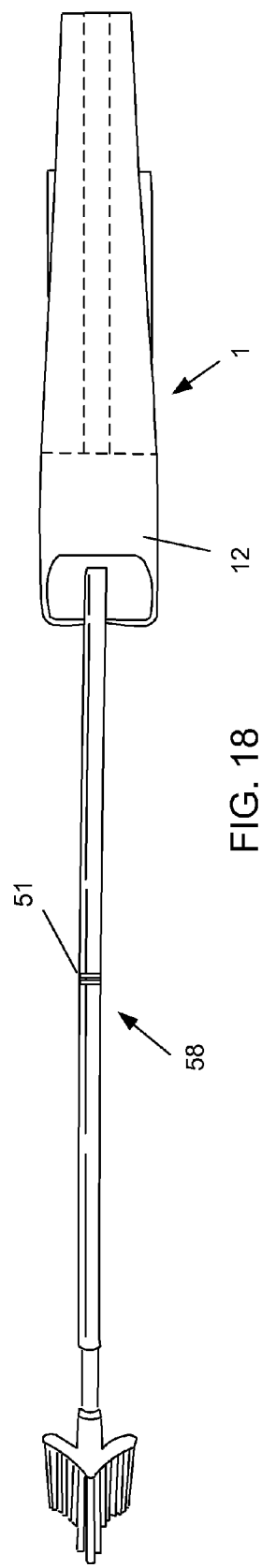
FIGS. 18-19 show another preferred embodiment of the present invention.
Figure 19:
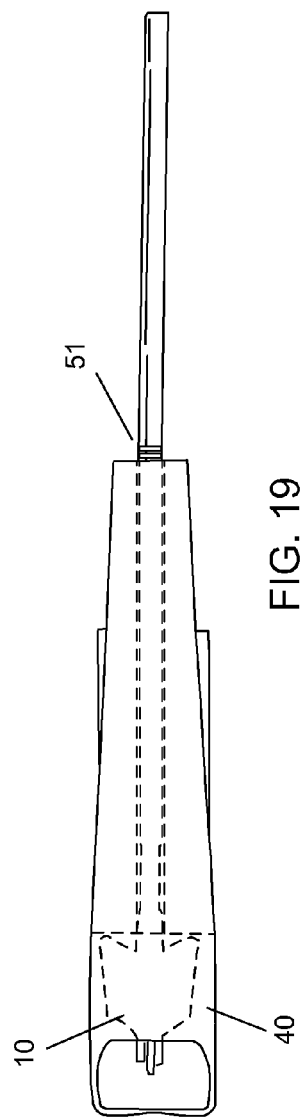

FIGS. 18 and 19 show another preferred embodiment of the present invention. Pap smear broom 58 includes indicator markings 51. As shown in FIG. 19, rearward stop indicator markings 51 alert the medical practitioner that broom head 10 is appropriately positioned within protective chamber 40. Once the medical practitioner realizes that broom head 10 is appropriately positioned within protective chamber 40, he will quit pulling rearward on Pap smear broom 58.

Although the above-preferred embodiments have been described with specificity, persons skilled in this art will recognize that many changes to the specific embodiments disclosed above could be made without departing from the spirit of the invention. Therefore, the attached claims and their legal equivalents should determine the scope of the invention.

What is claimed is:

1. A protective guide for attachment to an imaging transducer during a Pap smear, comprising:
   A. a cell extraction device, comprising:
      1. a cell extraction device head, and
      2. a head extension rod connected to said cell extraction device head, wherein said cell extraction device is either a Pap smear brush, a Pap smear broom or a Pap smear spatula,
   B. a cell extraction device access tunnel for receiving said cell extraction device and to allow for access and movement of said cell extraction device, wherein said head extension rod extends through said access tunnel and extends behind said access tunnel so that said head extension rod is hand-grabbed by an operator and moveable through said tunnel by hand operation of said operator,
   C. a cell extraction device protective chamber for covering and protecting said cell extraction device head as the cell extractive device is being inserted and removed from the patient's vagina, and
   D. a protective guide connector for removably connecting the protective guide to said imaging transducer,
   wherein the location of the cervix is determined by utilization of said imaging transducer, wherein an operator is able to hand-grasp said head extension rod and control said head extension rod to push said cell extraction device head outward from said protective chamber so that cell extraction device head contacts the cervix and removes cells from the cervix, wherein an operator is able to hand-grasp said head extension rod and control said head extension rod to pull said cell extraction device head back into said protective chamber after said cells have been removed from the cervix.

2. The protective guide as in claim 1, further comprising a head stop to halt the rearward motion of said cell extraction device as it is being pulled into said protective guide and to correctly locate said cell extraction device head within said protective chamber.

3. The protective guide as in claim 1, wherein said cell extraction device further comprises rearward stop indicator markings to halt the rearward motion of said cell extraction device as it is being pulled into said protective guide and to correctly locate said cell extraction device head within said protective chamber.

4. The protective guide as in claim 1, wherein said cell extraction device is a Pap smear brush.

5. The protective guide as in claim 1, wherein said cell extraction device is a Pap smear broom.

6. The protective guide as in claim 1, wherein said cell extraction device is a Pap smear spatula.

7. The protective guide as in claim 1, wherein said imaging transducer is an ultrasound probe.

8. The protective guide as in claim 1, wherein said protective guide connector is press fit onto said imaging transducer.

9. A method for protecting a cell extraction device during a Pap smear, comprising the steps of:
   A. inserting a cell extraction device into a protective guide, said cell extraction device comprising:
      1. a cell extraction device head, and
      2. head extension rod connected to said cell extraction device head, wherein said cell extraction device is either a Pap smear brush, a Pap smear broom or a Pap smear spatula,
   wherein said protective guide comprises:
      1. a cell extraction device access tunnel for receiving said cell extraction device and to allow for access and movement of said cell extraction device, wherein said head extension rod extends through said access tunnel and extends behind said protective guide so that said head extension rod is hand-grabbed by an operator and moveable through said tunnel by hand operation of said operator,
2. a cell extraction device protective chamber for covering and protecting said cell extraction device head as the cell extractive device is being inserted and removed from the patient's vagina, and
3. a protective guide connector for removably connecting the protective guide to said imaging transducer, B. hand-grasping said head extension rod to move said cell extraction device so that cell extraction device head is located within said protective chamber, C. connecting said cell extraction device to in imaging transducer, D. inserting said cell extraction device, said protective guide and said imaging transducer into the patient's vagina, E. determining the location of the cervix by utilization of said imaging transducer, F. hand-grasping said head extension rod to push said cell extraction device head outward from said protective chamber to contact the cervix, G. hand-grasping said head extension rod to remove cells from the cervix by utilization of said cell extraction device head, H. hand-grasping said head extension rod to pull said cell extraction device head back into said protective chamber, and I. removing said cell extraction device, said protective guide and said imaging transducer from the patient's vagina, wherein an operator hand-grabs said head extension rod during the entire Pap smear procedure.

10. The method as in claim 9, wherein said protective guide further comprises a head stop to stop the rearward motion of said cell extraction device as it is being pulled into said protective guide and to correctly locate said cell extraction device head within said protective chamber.

11. The method as in claim 9, wherein said cell extraction device further comprises rearward stop indicator markings to halt the rearward motion of said cell extraction device as it is being pulled into said protective guide and to correctly locate said cell extraction device head within said protective chamber.

12. The method as in claim 9, wherein said cell extraction device is a Pap smear brush.

13. The method as in claim 9, wherein said cell extraction device is a Pap smear broom.

14. The method as in claim 9, wherein said cell extraction device is a Pap smear spatula.

15. The method as in claim 9, wherein said imaging transducer is an ultrasound probe.

16. The method as in claim 9, wherein said protective guide connector is press fit onto said imaging transducer.

* * * * *